United States Patent
Peredo

(10) Patent No.: US 6,254,636 B1
(45) Date of Patent: *Jul. 3, 2001

(54) SINGLE SUTURE BIOLOGICAL TISSUE AORTIC STENTLESS VALVE

(75) Inventor: Mario Osvaldo Vrandecic Peredo, Belo Horizonte (BR)

(73) Assignee: St. Jude Medical, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/105,703

(22) Filed: Jun. 26, 1998

(51) Int. Cl.[7] ................................. A61F 2/24
(52) U.S. Cl. ............................... 623/2.15
(58) Field of Search .................. 623/2, 900, 2.12, 623/2.13, 2.14, 2.15, 2.16

(56) References Cited

U.S. PATENT DOCUMENTS

| | | |
|---|---|---|
| 3,656,185 | 4/1972 | Carpentier . |
| 4,172,295 | 10/1979 | Batten . |
| 4,218,782 * | 8/1980 | Rygg ........................ 623/2 |
| 4,388,735 | 6/1983 | Ionescu et al. . |
| 4,489,446 | 12/1984 | Reed . |
| 4,490,859 | 1/1985 | Black et al. . |
| 4,502,159 | 3/1985 | Woodroof et al. . |
| 5,554,184 | 9/1996 | Machiraju . |

FOREIGN PATENT DOCUMENTS

| | | |
|---|---|---|
| 0 143 246 A2 | 6/1985 | (EP) . |
| 0 338 994 | 10/1989 | (EP) . |
| WO 92/20303 | 11/1992 | (EP) . |
| 0 515 324 A1 * | 11/1992 | (EP) ........................ 623/2 |
| WO 97/25004 | 7/1997 | (EP) . |

OTHER PUBLICATIONS

Ross, "Aortic–Valve Replacement", The Lancet, Aug. 27, 1966, pp. 461–463.*

"Edwards Prima™ Stentless Bioprosthesis Modified Model 2500" Brochure, Sub–Coronary Implantation, and Trimming Technique, Edwards CVS Division, Baxter, Dec. of 1996.

* cited by examiner

Primary Examiner—David H. Willse
(74) Attorney, Agent, or Firm—Hallie A. Finucane, Esq.; Westman, Champlin & Kelly, P.A.

(57) ABSTRACT

A semilunar stentless valve is constructed entirely of biocompatible material, and has a plurality of leaflets that are joined to form an annulus and coapt to form a one-way valve. The leaflets open fully to minimize obstruction. A narrow rim strip overlies commissures where the leaflets join and around a base of the valve. The valve is of a conical design, flexible, easy to fit and preserves the integrity of the coronary sinuses. The valves can be implanted with a single suture row, reducing implant time significantly.

11 Claims, 5 Drawing Sheets

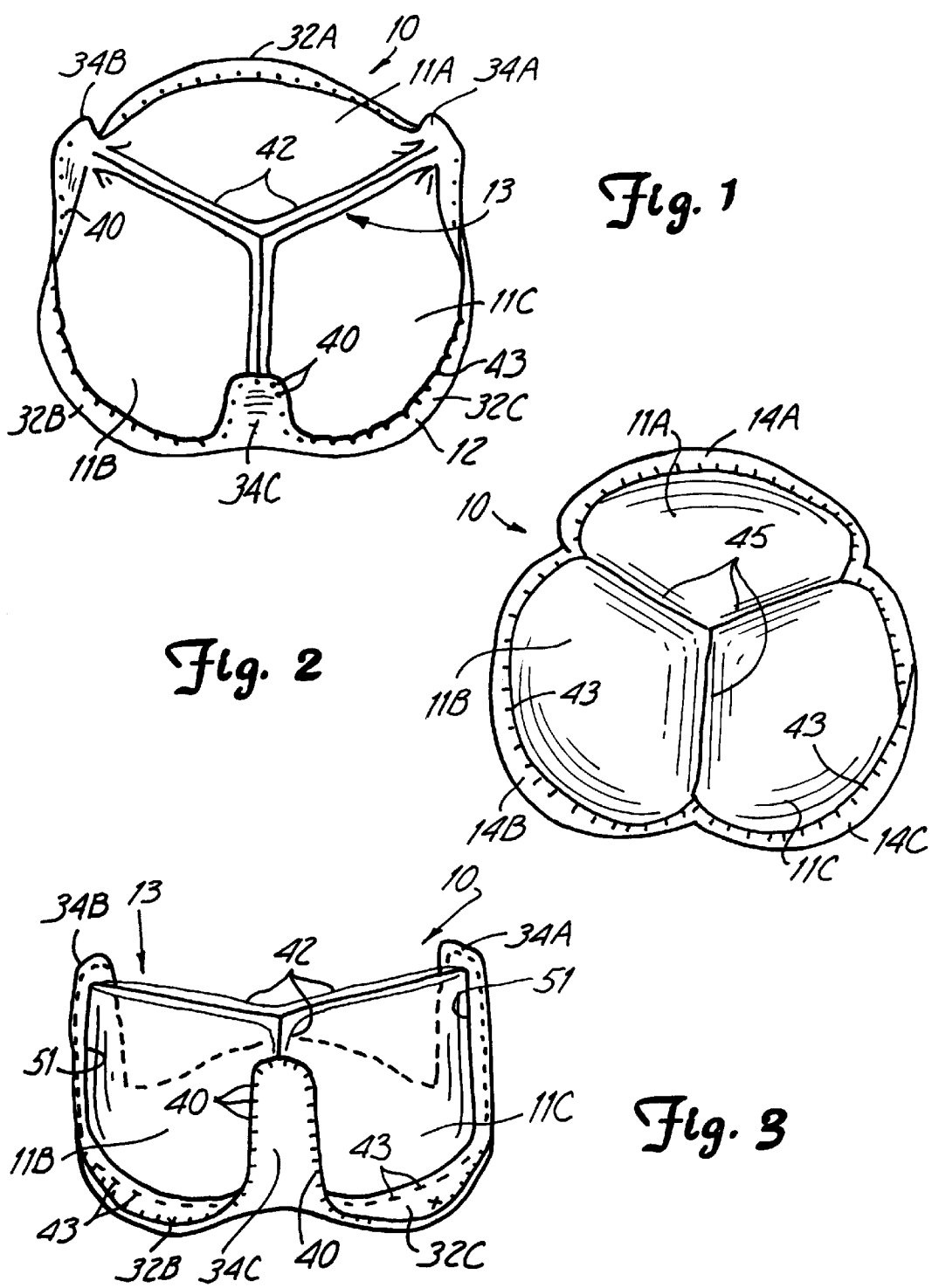

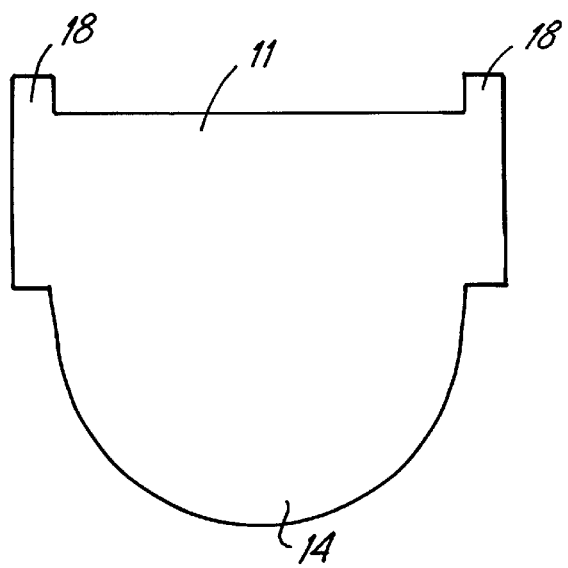
Fig. 4
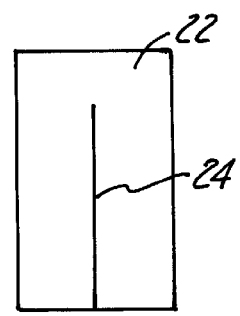
Fig. 5
Fig. 6
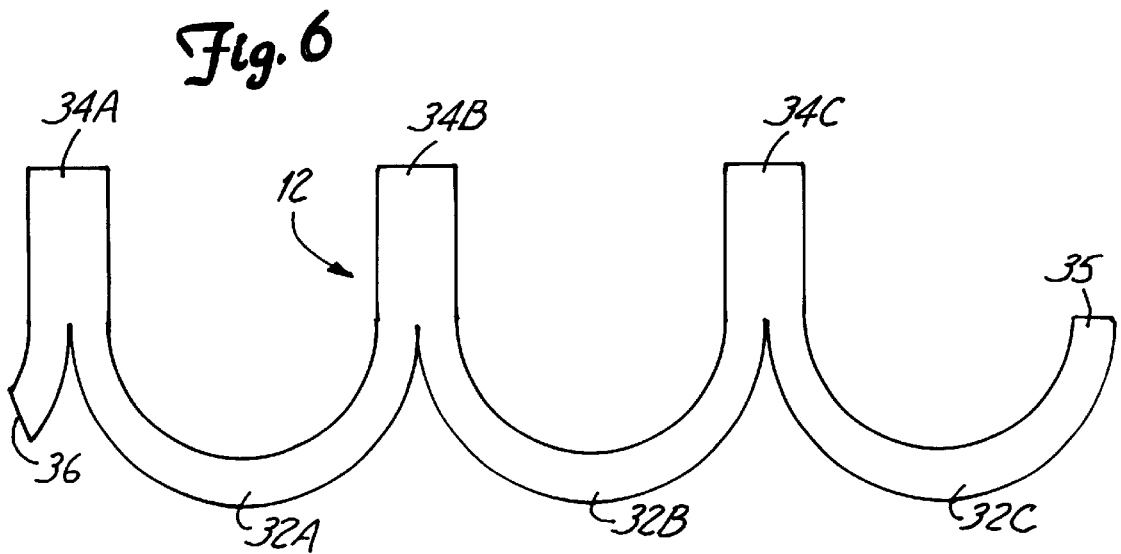

SINGLE SUTURE BIOLOGICAL TISSUE AORTIC STENTLESS VALVE

BACKGROUND OF THE INVENTION

The present invention relates to a stentless valve bioprosthesis constructed of single or multiple sections of biocompatible material tissue to minimize coronary obstruction. The valve is implantable with a single suture row.

Various stentless valves have been advanced. Tissue valves are typically used in those patients for whom long term anticoagulation is contraindicated, or who may be difficult to maintain on anticoagulation therapy. The stentless valves typically are constructed in a manner that requires a double row of sutures for fastening, one along an inflow edge and one along an outflow edge, and require a substantial amount of time for implanting.

Existing state-of-the-art valvular prostheses have one or more of the problems of introduction of foreign tissue, physical obstruction, and implantation trauma. The implantation trauma is accentuated when there is extensive suturing, for example, two suture rows.

Stentless aortic valves presently on the market have had problems because the valves have tall bodies, leading to obstruction of the coronary ostia or coronary sinuses, requirements for double suture rows, and extended implant times.

SUMMARY OF THE INVENTION

The present invention relates to an aortic or pulmonary stentless valve preferably constructed entirely of crosslinked biological tissue, which minimizes obstructions and permits implantation with a single suture row in significantly less time than that needed for implanting existing valves. The valve preferably is constructed of a single or of multiple pieces of bovine pericardial tissue. In a preferred form, multiple segments of tissue are formed in such a way to provide for complete coaptation of the valve leaflets to prevent regurgitation or insufficiency, and to provide full valve opening to allow for a maximum effective orifice area. The exterior of the valve is preferably conical in shape, which aids in implantation and reliability. The conical shape results in the valve being larger in diameter at the outflow end than at the inflow end.

The preferred form of the invention is an assembly of three leaflets of biological tissue that are attached to adjacent leaflets at the commissure region, preferably through the use of tissue reinforcing commissure posts and a separate reinforcing rim strip. The rim strip is sutured on the exterior of the leaflets when it is used and provides a suturing reinforcement at the perimeter or base of the valve. The suturing used for constructing or assembling the valve is on, or in, non critical areas of the tissue to enhance valve durability.

The biological commissure reinforcement posts or pads are sculpted to be applied at each commissure by slipping over adjoining edge portions of mating edges of the leaflets to strengthen the attachment and aid in the distribution of stresses at the critical areas where the adjacent valve leaflets join. The rim strip preferably is a biological tissue reinforcement that has portions sutured to the posts and leaflet edges at the commissural area of the leaflets, and sutured to the base edges of the leaflets, forming the base ring of the valve. The rim strip is on the outside of the leaflets, to provide reinforcement to the rim formed by the base ends of the leaflets, and thus aids in the attachment of the valve to the patient's annulus. The double layer of tissue at the rim provides a suture attachment site that is designed for strength. The design is anatomical in that it resembles the human aortic or pulmonary valve for a close fit, and needs only a single suture row for implantation. The low profile valve is short along the flow axis and of minimal width, so it is anatomically easy to handle.

Trimming biological tissue or other biocompatible material to the desired size and shape for constructing the valve can be done readily. The assembly of the valve parts requires minimal time, thereby reducing manufacturing costs. The implantation is easily carried out in significantly less time than that needed for existing prostheses.

Flexibility of the tissue leaflets and the reinforcement posts and rim in the commissure areas where the leaflets open and close permits a wide opening to thus reduce pressure drop across the valve once implanted. The valve leaflets are less prone to tear because of cushioning by the valve parts. The conical design and the flexibility of the tissue leaflets also ensures satisfactory leaflet coaptation to reduce any regurgitation or insufficiencies. Further, the fully flexible valve can be used in most aortic or pulmonary valve pathologies. The attachment rim fits all normal and abnormal annulus shapes for implantation.

The bovine biological aortic or pulmonary stentless valve of the present invention has an anatomical profile. The sewing cuff or rim is part of the leaflets and may include a reinforcing rim strip. It has a conic shape to be accommodated in most aortic or pulmonary geometries, and prevent valve insufficiency. The sewing area is easily penetratable with a needle, being no more than about 2 mm thick. The valve flexibility permits it to follow the contour of the patient's annulus, thus remaining beneath both coronary sinuses. The internal to external diameter ratio is excellent and better than present designs since the cuff or rim is not covered with fabric. The cuff or rim is an intrinsic part of the leaflets and follows the patient's annulus.

The present valve preferably is all biological and does not have synthetic material, such as a polyester cloth covering. The valve has a low commissural profile that simulates natural valve geometry. There is a need of only one suture row for implantation and while placing the sutures, the leaflets are preserved from needle injury since the components are all fully in the surgeon's view. The valve cuff or rim may be reinforced with a biological strip or tape without increasing the cuff or rim width or affecting the effective orifice area. The time of surgery is reduced significantly, and may be in the range of one-third to one-half of the implantation time required for existing valves. The reduced profile of the valve provides a superior view for the surgeon. This, in turn, helps in reducing implantation time, injury to leaflets, valve misalignment and occlusion of the ostia. Further, the problems associated with occlusion of the coronary sinuses is avoided, since the present valve leaves the coronary sinuses substantially unobstructed. Thus, situations caused by occlusions of the coronary sinuses or ostia are not likely to occur.

The valve can be offered with a specific holder, just as the existing replacement heart valves.

BRIEF DESCRIPTION OF THE DRAWINGS

FIG. 1 is an outlet end plan view of a stentless aortic valve made according to the present invention;

FIG. 2 is an inlet end plan view of the valve of FIG. 1;

FIG. 3 is a side view of the valve of FIG. 1;

FIG. 4 is a flat layout of a biocompatible material leaflet used for constructing the biological valve of the present invention;

FIG. 5 is a flat layout of a commissural biocompatible material post used for the assembly of leaflets shown in FIG. 4 into a valve;

FIG. 6 is a flat layout of a scalloped biological rim that is used for final assembly of the valve of the present invention;

DETAILED DESCRIPTION OF THE PREFERRED EMBODIMENTS

Figure 7:
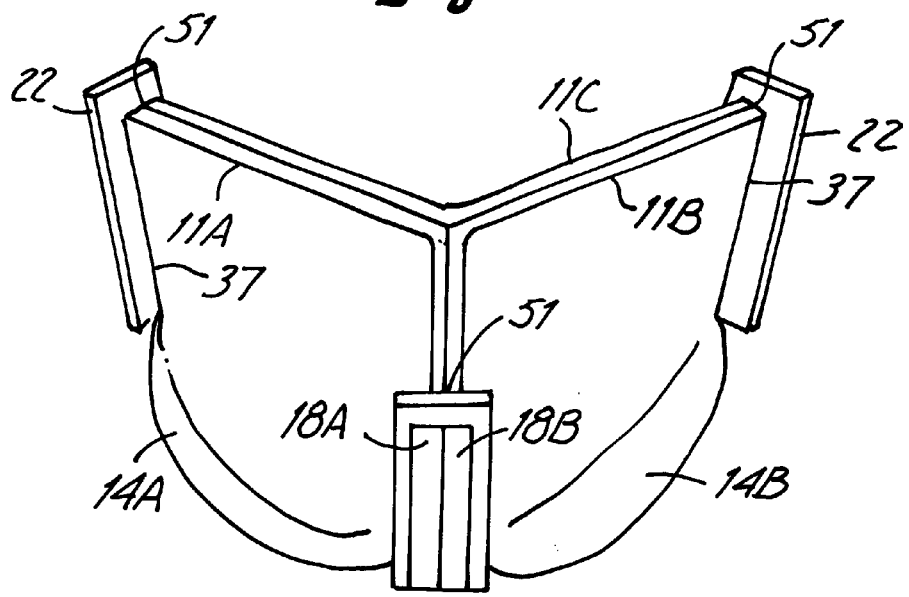
FIG. 7 is a perspective view of three leaflets being assembled using the reinforcing posts shown in FIG. 5.

FIGS. 1, 2 and 3 illustrate a biocompatible material prosthetic aortic valve assembly 10 which is a valving element and which has an outflow end 13 shown in FIG. 1. While the invention is described in reference to aortic valves, the invention is applicable to semilunar valves, including the pulmonary valve. The valve assembly is made of three leaflets 11A, 11B, 11C. A scalloped, narrow rim strip 12 may be sutured around the periphery of the base of the valve assembly and along the commissure regions of the leaflets.

The biocompatible material for the leaflets, rim strip and posts includes both biological material or synthetic polymers which could be either naturally occurring or artificially produced.

Biological tissue for use in this invention includes relatively intact tissue as well as decellularized or otherwise modified tissue. These tissues may be obtained from, for example, heart valves, pericardial tissue, dura mater, small intestine submucosa, fascia, skin or any other membranous tissue. Preferably, the biological tissue is bovine pericardial tissue. The biological tissue is selected to have strength and flexibility. The tissue for the leaflets, posts and rim is selected to avoid thin spots. Generally, the biological tissue is composed of collagen-containing structures derived from a particular animal species, typically mammalian, such as human, bovine, porcine, equine, seal, or kangaroo, as well as engineered tissues. Engineered tissue typically involves repopulated matrices which can be derived from the tissues mentioned above or synthetically fabricated. The biological tissue may be fixed to cross-link the tissue and provide mechanical stabilization by preventing enzymatic degradation of the tissue, although the matrices do not necessarily need to be fixed. Glutaraldehyde is typically used to fix the material, but other fixation methods, such as epoxides, other difunctional aldehydes, or photooxidation can be used.

Synthetic, biocompatible materials for use in the prosthesis of the present invention include synthetic polymers as well as biological polymers. Synthetic, biocompatible materials for use in the prosthesis include synthetic polymers as well as biological polymers. Synthetic polymers include polyamides(nylon),polyesters,polystyrene, polyacrylates, vinyl polymers (e.g. polyethylene, polytetrafluoroethylene, polypropylene and polyvinylchloride), polycarbonate, polyurethane, polydimethyl siloxane, cellulose acetate, polymethyl methacrylate, ethylene vinyl acetate, polysulfone, and similar copolymers. Biological polymers include natural forms such as collagen, elastin and cellulose or purified biopolymers such as polyaminoacids or polysaccharides. All of these materials can be used singularly or in a combination thereof and can be molded or cast into the selected forms or can be knit or woven into a mesh to form a matrix.

The size of the leaflets will depend on the size of the valve that needs repair, and can be selected as desired by manufacturers. Because the valve assembly has no stent, and is very flexible, valve size is capable of being formed to fit a wide range of orifice sizes and shapes. Preferably, the leaflets comprise bovine pericardial tissue.

FIGS. 4–6 show the preferred form of the invention in flat layout. Each of the leaflets shown generally at 11 has a commissure mounting ear 18 on each side. The leaflets 11A–11C are held together at each commissure with a separate commissural post 22, also preferably made of bovine pericardial tissue, as shown in FIG. 5. Each post 22 has a slit 24 sized to slip over two thicknesses of leaflets at the commissure of two adjoining leaflets. The slit 24 permits sliding a post 22 over the edges of two adjoining leaflets to the interior of the commissural mounting ears 18 of the leaflets. The ears or edge portions 18 are positioned outwardly from the commissure posts and fold flat against the posts 22 on the exterior of the slits 24, as shown in FIG. 7. There are three such posts 22 used when a three-leaflet valve is to be assembled, one at each commissure.

The rim strip 12 shown in FIG. 6 in flat layout is formed from a single piece of biocompatible material as described above, preferably bovine pericardial tissue, in a scalloped shape to provide for suture attachment. The rim strip 12 has three scalloped rim strip portions 32A–32C joined by commissure post cover sections 34A–34C between the scallops. The flat layout shown in FIG. 6 indicates the end scallop 32C is terminated along a line 35, which will join with the line 36 at the left-hand side of the figure when the rim strip 12 is formed into an annulus for assembling the valve.

To assemble the valve, the three leaflets shown at 11A, 11B and 11C are joined to form an annulus with the ear portions 18 in contact with the edge or ear portions 18 of the next adjacent leaflet to form two thicknesses of tissue. As shown, ear portion 18A on one side of the leaflet 11A is contiguous with the ear portion 18B of the adjacent leaflet 11B (see FIG. 7). The slit 24 of one commissural post 22 is slid over the contiguous edge of the leaflets, with the ears 18A and 18B to the exterior.

The opposite side ear portion 18A of leaflet 11A is placed contiguous with one side ear portion 18C of the leaflet 11C, and preferably a commissural post 22 is slipped in place over the two thicknesses of tissue. The ear portions 18B and 18C on the opposite side of the respective leaflets that are not attached are then placed contiguous as well and the third commissural post 22 is slid over the final commissure. Each one of the commissures, formed by joining the three leaflets, is provided with a post 22, shown in position in FIG. 7. The ears 18A and 18B are shown after they have been folded back onto the side portions of the posts 22.

Figure 8:
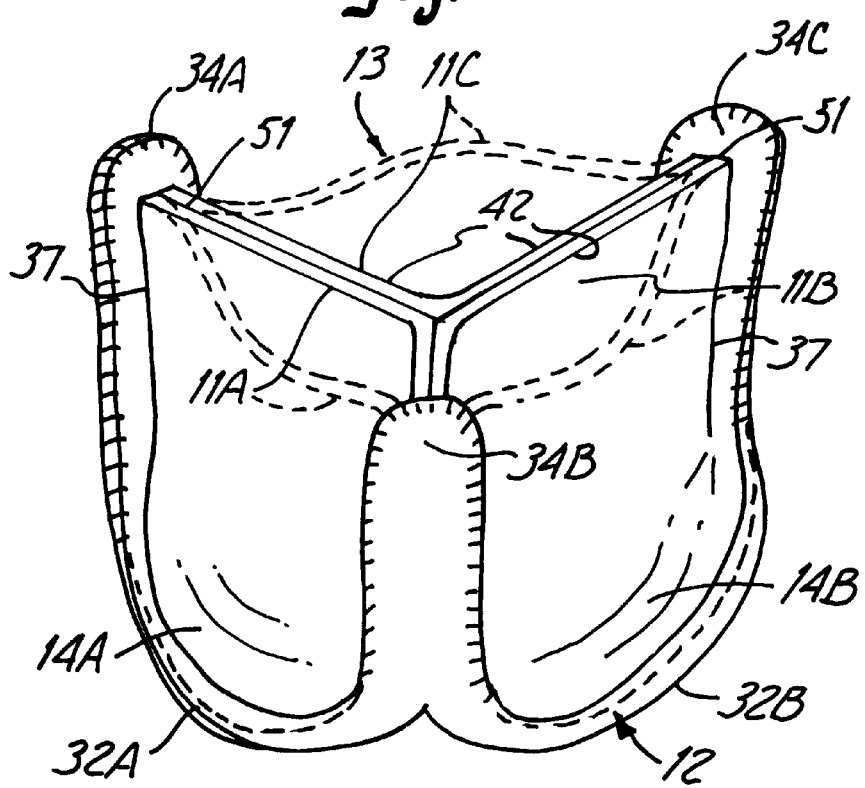
FIG. 8 is a further perspective view showing the valve of the present invention when the biological rim shown in FIG. 6 is placed around the leaflet assembly, just prior to suturing the components to make the valves shown in FIGS. 1–3.

FIG. 8 illustrates the next step in assembly, when the rim strip 12 is positioned so that each one of the reinforcement posts 34A, 34B, and 34C is overlying the ears 18 and posts 22 at each of the commissures between adjacent valve leaflets. The scalloped portions of rim strip 12 rest on the rounded base ends 14A–14C of the leaflets to form a second layer of tissue at the base or inflow end of the valve. The base ends of the leaflets may be used as a sewing cuff or rim, without the reinforcing rim strip 12.

The next step is to suture the scalloped shaped rim strip 12 to the leaflet and post assembly. The sutures pass through adjacent (underlying) portions of the biocompatible material forming the leaflets 11, in particular the base ends 14A–14C and posts 22. In FIGS. 7 and 8, it can be seen that the junction of the leaflets with the posts 22 and reinforcement posts 34A–34C of the rim strip 12 form edges 37 that extend upwardly. When the rim strip 12 is in place, it provides an encircling, shaping rim and the outflow ends or edges 42 of the leaflets will tend to move toward the center and contact each other so that they coapt at the outlet or outflow end. The lower rounded base portions 14A–14C of the leaflets extend around the inflow end and form an implantation cuff or base. The scalloped rim strip portions 32A, 32B and 32C coupled with the exterior surface of the base portions 14A–14C form a double layer of biocompatible material at the site of the suture attachment. All suturing of leaflets in the assembly of the valve is placed in areas of low stress to enhance durability of the valve, such as commissural areas 51 or outflow ends 42.

As shown in FIG. 3, the posts 34A, 34B and 34C of the rim strip 12 are also sutured to the posts 22 and the ears 18 of the leaflets with a suture that overlaps the edges of the rim posts 34A–34C and overlap the commissures to insure there is no leakage. The sutures around the periphery of the commissural posts not only can loop over the edge, as shown at 40 but can be passed through the ears 18 to insure a seal at the commissure. The rim strip portions 32A–32C are also sutured to the edges of the curved base portions 14A, 14B and 14C as shown at 43.

The outflow ends 42 of the leaflets 11A–11C have generally straight edges, which will move apart or open under pressure from the inflow end of the valve 10, to expand to the full diameter permitted by the three leaflets. Upon any reverse flow or back pressure, the leaflets will close tightly to avoid regurgitation at the inflow commissures, as shown at 45 in FIG. 2. The mating outflow ends of the leaflets will fold together for accommodating changes in valve diameter and continue to close tightly.

The stentless valve of the present invention is preferably all tissue (biomaterial), so it is flexible and can be fitted into place in the annulus. However, it is within the contemplation of the invention to use synthetic or biological polymers for all or a portion of the valve. The rim strip 12 provides a bounding reinforcement along the curved leaflet base ends 14A–14C. The leaflets can be made of one single piece or three separate pieces of the biocompatible materials described above (biological or engineered tissue, or biological or synthetic polymers). No synthetic sewing cuff is added. The same leaflet material serves as a sewing cuff or rim which is reinforced by the rim strips portions 32A–32C without decreasing effective orifice area. The ratio between internal and external diameter is superior to existing valves because there is no requirement for a fabric sewing ring or cuff or a stent.

Figure 9:
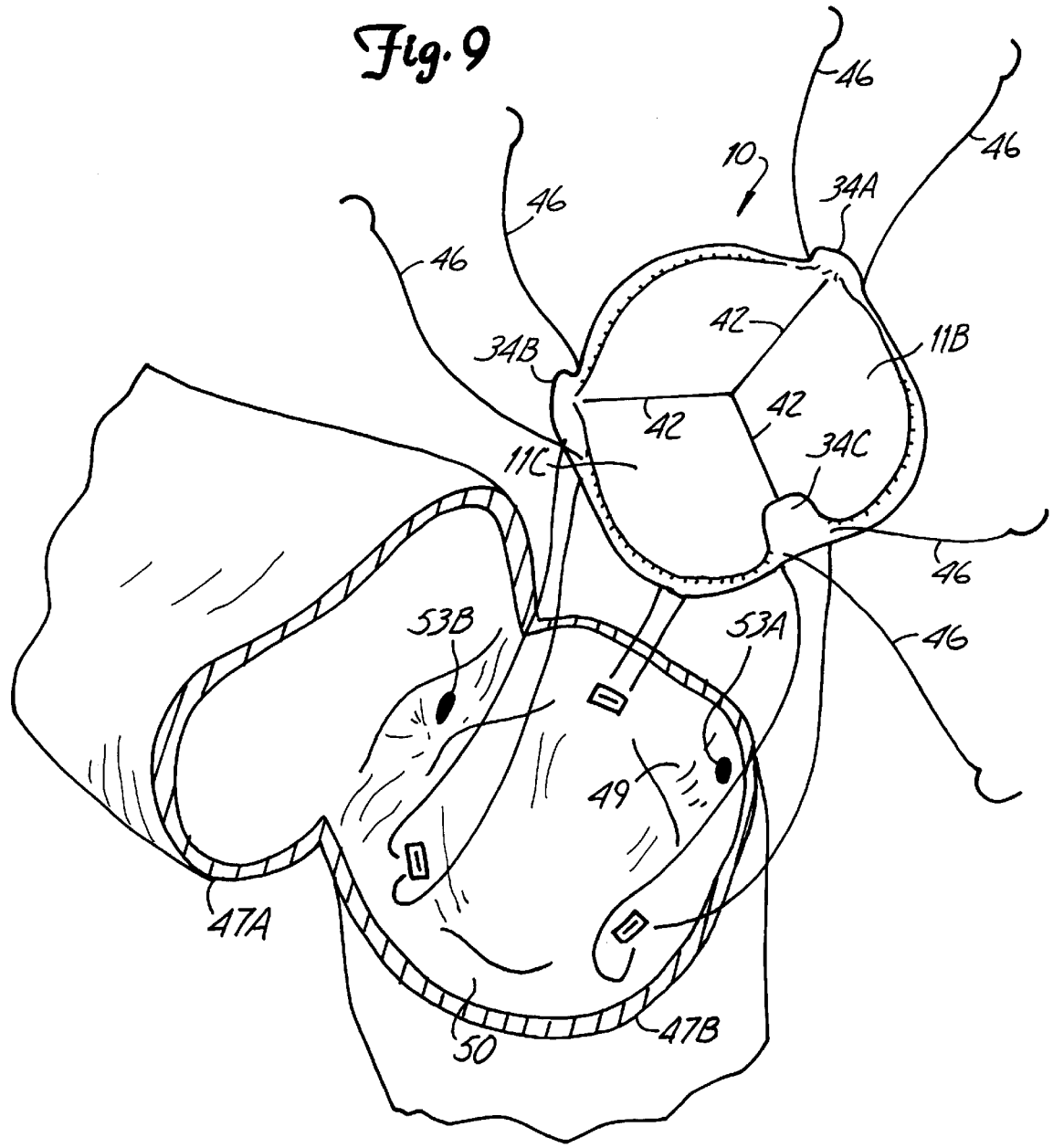
FIG. 9 is a perspective schematic representation of the valve of the present invention being implanted with parts broken away.

As shown in FIG. 9, the base of the valve prosthesis will be positioned internally of the heart tissue forming the aortic rim 49 after necessary excising of the diseased valve, and complete decalcification of the heart annulus. The valve assembly 10 is made to have a conical shape. The annular diameter of the base is smaller (in models about 4 mm less) than the outflow end diameter, which makes valve stenosis or insufficiency insignificant. The valve will fit in most pathologies of the aortic or pulmonary valve. The top half of the valve can be expanded because the valve leaflets have redundant coaptation.

The aortotomy has been completed and the natural valve leaflets excised in FIG. 9. FIG. 9 shows the left coronary artery 53B and the right coronary artery 53A. As shown in FIG. 9 one may use an interrupted suture, depending on the patient's annular tissue quality. These single commissural sutures are shown and these same sutures can be used for suturing of the valve rim to the patient's annulus, using a single suture row. A single suture can be started between the commissure lines along the biological rim 12, and the valve 10 is sutured into place easily. The suture used for implantation is illustrated at 46 in FIG. 9, which schematically illustrates the valve 10 positioned prior to implantation and shows initial attachment to the heart aortic rim tissue 50.

Since the prosthesis is preferably made entirely of tissue, and has no stent or artificial material sewing ring, it can be manipulated to fit most semilunar valve pathologies. The suturing of the prosthesis can commence generally at one of the commissures. The base end portions 14 (including portions 14A and 14B) of the leaflets curve outwardly from a valve flow axis and form the base of the sewing rim so the inlet size is maximized to increase the effective orifice area between the posts which are sutured directly to heart tissue at the annulus, schematically shown in FIG. 9. The curved base end portions 14 of the leaflets provide a smooth flow profile. Since there is a double layer of biocompatible material at the sewing rim of the valve, including the rim strip 12 and the curved base end portions 14 of the leaflets, the valve 10 is secured reliably. Also curving the leaflets to form a base for the sewing rim aids in maintaining a low profile valve. The axial distance or length required for the sewing rim is greatly reduced. Also, in this valve, the posts at the commissures are narrower in width than other tissue valves. These features aid in achieving the advantages of reducing implantation time, injury to leaflets, valve misalignment and occlusion of the ostia.

The posts 34A–34C support the commissures of the leaflets 11A–11C without impinging or obstructing the right and left coronary sinuses. The tissue 50 forming the annulus can be sutured directly to the perimeter of the posts 34A–34C and rim portions 32A–32C with a single suture row. A continuous stitch, a set of interrupted sutures, or a combination, in a single row is used up around the post as shown at 55, over the top of each commissure region of the leaflets and then down to extend around the partially circular portions of the base of the leaflets where the attachment is directly to the heart tissue 50. Knots 45 are made to anchor the suture segments (see FIG. 10).

Since the entire valve is made of a flexible biocompatible material, there is a full flow diameter at the aortic orifice at the inflow end, as can be seen in FIG. 2. There are no rigid parts to cause nooks or crannies that can produce local stasis of blood that may lead to thrombus formation. Further, since there is no sewing cuff, healing can take place directly between the implanted tissue and the body tissue, and this provides for less likelihood of failures of sutures. The valve is short along the flow axis and thus anatomically easy to handle.

Figure 10:
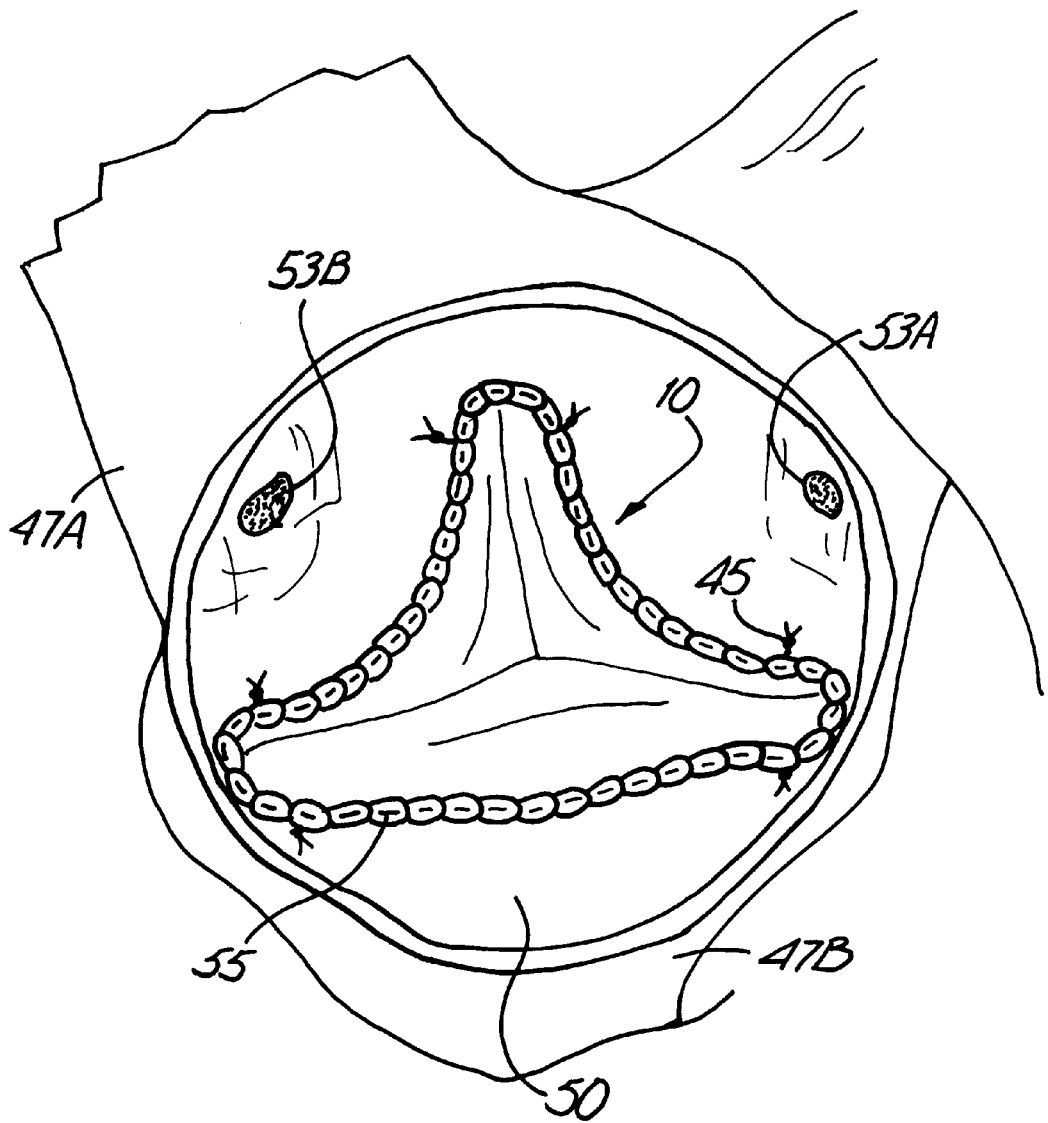
FIG. 10 is a plan view of the valve of the present invention after it has been implanted.

As shown schematically in FIG. 10 the coronary sinus region around arteries 53A and 53B are not impinged by the valve 10 when implanted.

The inflow of blood into the valve will cause the leaflets 11A–11C to separate fully, against the aortic wall, with no sharp edges, pockets or the like, and the valve design insures that there is no interference with the coronary sinuses or ostia. Because the leaflets are flexible biocompatible materials, they will close to prevent reverse flow with very little leakage. Thus the valve 10 closes with low diastolic pressure.

Using one suture row as shown at 55 in FIG. 10 provides better hemodynamics and good durability. The single suture row does not impinge on the coronary sinuses or ostia. The valve 10 has an excellent interior to exterior size ratio for better hemodynamics.

The stentless valve 10 is fully flexible and is thus easier to fit for implant. The valve will conform to the shape of the annulus and lumen of the aorta without distending the patient's tissue or placing undue stress on the suture attachments. The valve mimics operation of the natural valve when implanted.

The leaflets coapt easily to provide the one-way check valve, and they open fully to avoid restriction of outflow, with a low pressure drop.

Although the present invention has been described with reference to preferred embodiments, workers skilled in the art will recognize that changes may be made in form and detail without departing from the spirit and scope of the invention.

What is claimed is:

1. A stentless valve prosthesis made entirely of biological tissue comprising a sheet form of biological tissue cut to provide a plurality of leaflets, each leaflet having edges joined to edges of other leaflets to encircle a flow opening and form a flow passage, the edges extending in a direction along the flow passage and outflow ends of the leaflets being of size to coapt to form a valve, and a narrow rim strip of biological material sutured to the leaflets around an inflow end, the narrow rim strip having post portions extending along commissures formed where the edges of adjacent leaflets join, and overlying and being sutured to the leaflets along the commissures.

2. The valve of claim 1, wherein the plurality of leaflets comprises three leaflets to form a valve, the rim strip comprising a narrow rim of tissue along the inflow end, the leaflets having base peripheries smoothly curved outwardly around a base at the inflow end.

3. The valve of claim 1, wherein an outflow end of the valve has a larger diameter than the inflow end to form a conical shape.

4. A stentless valve prosthesis made entirely of biological material comprising a plurality of leaflets having edges joined along commissures to encircle a flow opening and of size to coapt to form a valve, a separate commissure post supporting leaflets joined at each commissure, a rim strip sutured to the leaflets around an inflow end, the rim strip having a rim post portion extending along each commissure post and sutured to the leaflets and to the commissure posts where adjacent leaflets join.

5. The valve of claim 4, wherein each commissure post has a slot in which mating edges of two adjacent leaflets are positioned, the rim post portions being sutured to ends of the leaflets extending through the respective slot to an exterior of the commissure post.

6. The valve of claim 4, wherein said commissure posts and rim post portions extend in the direction of flow beyond edges of the leaflets at an outflow end.

7. The valve of claim 4, wherein said leaflets are individually formed, and have leaflet portions that extend to an exterior from the commissure posts, said leaflet portions being covered by the rim post portions when the rim post portions are sutured to the commissure posts.

8. A stentless tissue valve prosthesis, comprising a plurality of three substantially identically constructed leaflets of biological tissue, said leaflets having outflow edges at outflow ends that are substantially straight, and inflow edges that are curved, each leaflet being joined to two other leaflets along commissures extending from an inflow end to an outflow end, thereby forming an interior flow passage, the outflow ends of said leaflets coapting to prevent reverse flow, the curved inflow edges of the leaflets forming a rim for attachment to tissue, a reinforcing strip of biological tissue along the curved inflow edges of the leaflets on an exterior of the leaflets to form a suture reinforcement along the rim, and a separate strip of biological tissue at each commissure secured to hold adjacent leaflets forming the commissures together, a periphery of the valve being defined by the leaflets and the separate strips at each commissure.

9. A stentless tissue valve prosthesis, comprising a plurality of three substantially identically constructed leaflets of biological tissue, said leaflets having outflow edges at outflow ends that are substantially straight, and inflow edges that are curved, each leaflet being joined to two other leaflets along commissures extending from an inflow end to an outflow end, thereby forming an interior flow passage, the outflow ends of said leaflets coapting to prevent reverse flow, the curved inflow edges of the leaflets forming edge portions for attachment to tissue, a plurality of commissure posts, one for each commissure, each commissure post comprising a post of biological tissue having a longitudinal slit therein, said slit being of size to receive two thicknesses of leaflet tissue at a respective commissure, to form a commissure junction between the leaflets, a rim secured to the edge portions of the leaflet and having rim post portions sutured to the commissure posts, the commissure posts and rim post portions being spaced apart so the leaflets are free to move outwardly between the rim post portions.

10. A stentless valve prosthesis comprising a plurality of leaflets having edges joined to encircle a flow opening and of size to coapt to form a valve having commissures formed where adjacent leaflets join, a tissue post sutured at each commissure, the leaflets having base portions curving outwardly from a central axis between the commissures to form an inflow end, and the base portions forming at least a part of a sewing rim for the valve.

11. The stentless valve prosthesis of claim 10, wherein the tissue is bovine pericardial tissue.

* * * * *